(12) United States Patent
Notohara et al.

(10) Patent No.: US 8,798,231 B2
(45) Date of Patent: Aug. 5, 2014

(54) RADIOGRAPHIC APPARATUS

(75) Inventors: Daisuke Notohara, Kyoto (JP); Koichi Shibata, Otsu (JP)

(73) Assignee: Shimadzu Corporation, Kyoto (JP)

( * ) Notice: Subject to any disclaimer, the term of this patent is extended or adjusted under 35 U.S.C. 154(b) by 366 days.

(21) Appl. No.: 13/387,232

(22) PCT Filed: Jul. 21, 2010

(86) PCT No.: PCT/JP2010/004677
§ 371 (c)(1),
(2), (4) Date: Jan. 26, 2012

(87) PCT Pub. No.: WO2011/013328
PCT Pub. Date: Feb. 3, 2011

(65) Prior Publication Data
US 2012/0128119 A1    May 24, 2012

(30) Foreign Application Priority Data
Jul. 27, 2009   (WO) ................. PCT/JP2009/003531

(51) Int. Cl.
*A61B 6/00* (2006.01)
(52) U.S. Cl.
USPC .......................................................... 378/22
(58) Field of Classification Search
USPC ........... 378/10, 19, 21–27, 98.8, 98.11, 98.12
See application file for complete search history.

(56) References Cited

U.S. PATENT DOCUMENTS

| | | | |
|---|---|---|---|
| 7,940,887 | B2 | 5/2011 | Shibata et al. |
| 2006/0104417 | A1 | 5/2006 | Kameshima et al. |
| 2008/0101537 | A1 | 5/2008 | Sendai |

FOREIGN PATENT DOCUMENTS

| | | |
|---|---|---|
| JP | 2006-68512 A | 3/2006 |
| JP | 2006-271513 A | 10/2006 |
| JP | 2008-104673 A | 5/2008 |
| JP | 2008-167854 A | 7/2008 |
| WO | WO-2008/018510 A1 | 2/2008 |

OTHER PUBLICATIONS

International Search Report for the Application No. PCT/JP2010/004677 mailed Oct. 19, 2010.

*Primary Examiner* — Courtney Thomas
(74) *Attorney, Agent, or Firm* — Cheng Law Group, PLLC

(57) ABSTRACT

One object of this invention is to provide radiography apparatus with suppressed exposure to a subject in tomography mode. An FPD provided in X-ray apparatus according to this invention converts X-rays into electric signals, and thereafter amplifies the signals to output them to an image generation section. According to this invention, an amplification factor is higher in a tomography mode than in a spot radiography mode. A tomographic image is obtained through superimposing two or more fluoroscopic image. In comparison of the fluoroscopic images, they differ from one another in appearance of the false image. Accordingly, superimposing the images may achieve cancel of the false images. In this way, the tomographic image finally obtained has no false image.

10 Claims, 11 Drawing Sheets

Fig. 6
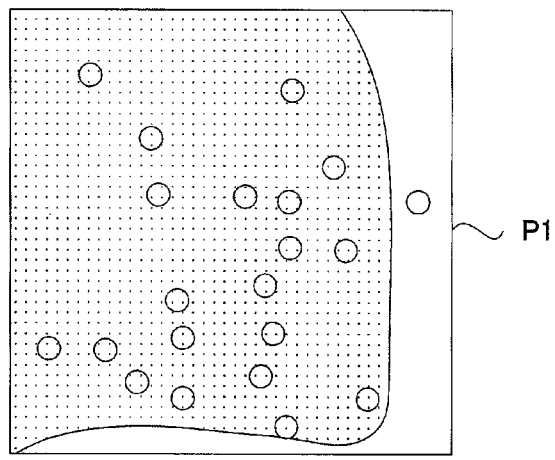
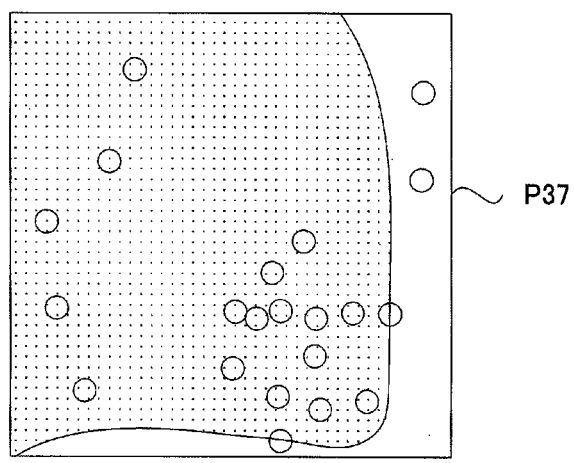
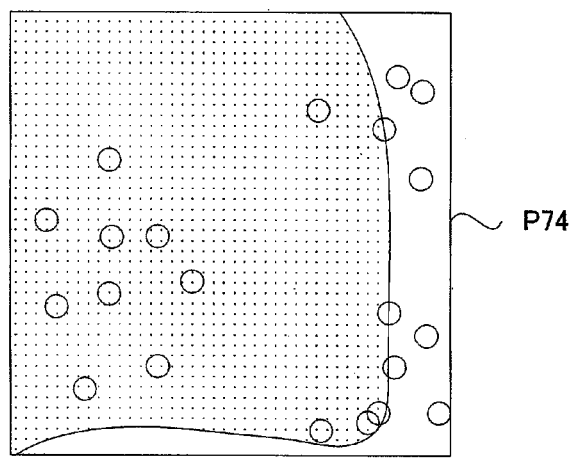

RADIOGRAPHIC APPARATUS

TECHNICAL FIELD

This invention relates to radiographic apparatus provided with a radiation source and an FPD. In particular, this invention relates to radiographic apparatus that allows selection of any one of a tomography mode and a spot radiography mode. In the tomography mode, a series of fluoroscopic images are taken while the radiation source and the FPD moves synchronously in opposite directions to each other, and the images are superimposed to obtain a sectional image of a subject. In the spot radiography mode, a single fluoroscopic image is taken through irradiating with single shot radiation.

BACKGROUND ART

Medical institutions are equipped with radiographic apparatus 51 for obtaining a tomographic image of a subject M. Such radiographic apparatus 51 includes a configuration in which a radiation source 53 that emits radiation and an FPD 54 that detects radiation move synchronously to continuously take a series of fluoroscopic images, and then the series of fluoroscopic images are superimposed to obtain the sectional image (see FIG. 13.) In such radiographic apparatus 51, during taking a series of fluoroscopic images, the radiation source 53 and the FPD 54 move along a body axis direction A of the subject M as to approach to each other, thereby having the same position in the body axis direction A. Thereafter, the radiation source 53 and the FPD 54 move along the body axis direction A as to be spaced away from each other. Such radiographic apparatus is described, for example, in Patent Literature 1.

Description will be given of operation in taking the sectional image as above. Firstly, the radiation source 53 intermittently emits radiation while moving. Specifically, the radiation source 53 moves along the body axis direction of the subject M for every completion of irradiation, and again emits radiation. In this way, 74 fluoroscopic images are obtained, and then superimposed. The finished image is a tomographic image having a sectional image appearing when the subject is cut along a sectional plane.

The radiographic apparatus 51 may also take a radioscopic image that simply visualizes the subject M through various settings. For obtaining such radioscopic image in this way, the radiation source 53 and the FPD 4 each move into a given position. During this movement, a fluoroscopic image is once taken while the subject M is placed. Such radiography is referred to as spot radiography as distinction from tomography.

Next, description will be given of how the FPD 4 detects radiation emitted from the radiation source 53. Radiation entering the FPD 4 is once converted into an electric signal and amplified by a given magnification. Thereafter, the electric signal is converted into a digital signal. This amplification factor corresponds to an analog gain. It is necessary to irradiate a subject with a certain dose of radiation for obtaining a radioscopic image suitable for diagnosis. It is assumed that an extremely low dose of radiation is applied for suppressing exposure radiation to the subject. In this case, as an analog gain increases by a decreased dose of radiation, a noise component contained in the electric signal is also amplified. Accordingly, a granular false image is to be contained in the radioscopic image acquired. On the other hand, the radioscopic image has a reduced contrast, since an electric signal is not sufficiently amplified unless an analog gain increases. As noted above, the conventional configuration is set to have an analog gain not more than a certain value and a dose of radiation not less than a certain value in order to prevent reduction in visibility of the radioscopic image.

[Patent Literature 1] Japanese Patent Publication No. 2006-271513

DISCLOSURE OF THE INVENTION

Summary of the Invention

The conventional configuration, however, has the following problem. That is, the conventional configuration has a problem that the subject is exposed to a higher dose of radiation in the tomography mode. On the other hand, radiation is once applied in the spot radiography. In the spot radiography, however, two or more fluoroscopic images are taken for tomography, and thus the subject is exposed to a higher dose of radiation. Assumed that 74 fluoroscopic images are obtained during the tomography, an exposure radiation in tomography is 74 times an exposure, radiation in the spot radiography.

This invention has been made regarding the state of the art noted above, and its object is to provide radiographic apparatus having suppressed exposure radiation to a subject in a tomography mode.

Means for Solving the Problem

This invention is constituted as stated below to achieve the above object. That is, radiographic apparatus according to this invention includes a radiation source, a radiation source controlling device, a radiation detecting device, a moving device, an image generation device, and a superimposing device. The radiation source emits radiation. The radiation source controlling device controls output of radiation. The radiation detecting device detects radiation. The moving device moves the radiation source and the radiation detecting device synchronously. The image generation device generates a fluoroscopic image based on a detection signal from the radiation detecting device. The superimposing device superimposes a series of fluoroscopic images continuously taken while the radiation source and the radiation detecting device moves or superimposes an identical site of the subject in the series of fluoroscopic images one another, thereby generating a tomographic image. The radiation detecting device includes (A) a radiation conversion device for converting radiation entering the radiation detecting device into an electric signal, and (B) an amplifying device for amplifying the electric signal by a given amplification factor. Here, let an imaging mode where the radiation detecting device is irradiated with single shot radiation to obtain a single fluoroscopic imaging be a spot radiography mode, and an imaging mode where a tomographic image is obtained be a tomography mode, an amplification factor is higher in the tomography mode than in the spot radiography mode, and output of single-shot radiation from the radiation source is less in the tomography mode than in the spot radiography mode.

[Operation and Effect]

The radiographic apparatus according to this invention may select the spot radiography mode or the tomography mode. Moreover, the radiation detecting device provided in the radiographic apparatus according to this invention converts radiation into an electric signal, and thereafter amplifies the signal to output it to the image generation device. In the conventional configuration, an electric signal is amplified by a given amplification factor regardless of the imaging modes. According to this invention, an amplification factor is higher in the tomography mode than in the spot radiography mode. Consequently, a fluoroscopic image obtained in the tomography mode has higher contrast even when radiation intensity is suppressed in the tomography mode.

Generally, an increased amplification factor may lead to an amplified noise component superimposed on the electric signal. When a fluoroscopic image is obtained with the radiographic apparatus of this invention, a false image due to noise components will surely appear with ease. On the other hand, a tomographic image is obtained through superimposing one another a series of fluoroscopic images or an identical site of the subject in the series of fluoroscopic images. In comparison of the fluoroscopic images, they differ from one another in appearance of the false image. Accordingly, superimposing the images may achieve cancel of the false images. In this way, the tomographic image finally obtained has no false image. The fluoroscopic images differ from one another in appearance of the false image because the noise component superimposed on the electric signal varies temporally and two or more fluoroscopic images are each obtained with different timing.

Since the spot radiography is conducted with a low amplification factor as usual, the fluoroscopic image in the spot radiography is clear with no false image appearing therein.

Moreover, the radiographic apparatus according to this invention includes a radiation source, a radiation source controlling device, a radiation detecting device, a moving device, an image generation device, and a superimposing device. The radiation source emits radiation. The radiation source controlling device controls output of radiation. The radiation detecting device detects radiation. The moving device moves the radiation source and the radiation detecting device synchronously. The image generation device generates a fluoroscopic image based on a detection signal from the radiation detecting device. The superimposing device superimposes a series of fluoroscopic images continuously taken while the radiation source and the radiation detecting device moves or superimposes an identical site of the subject in the series of fluoroscopic images one another, thereby generating a tomographic image. The radiation detecting device includes (A) a radiation conversion device for converting radiation entering the radiation detecting device into an electric signal, (B) an amplifying device for amplifying the electric signal by a given amplification factor, and (C) an amplification factor setting device for setting an amplification factor of the amplifying device in accordance with an imaging mode upon imaging, here letting an imaging mode that irradiates the radiation detecting device with single shot radiation to obtain a single fluoroscopic imaging be a spot radiography mode and letting an imaging mode that obtains a tomographic image be a tomography mode. The amplification factor setting device sets an amplification factor in the tomography mode higher than that in the spot radiography mode. The radiation source controlling device sets output of single-shot radiation from the radiation source less in the tomography mode than in the spot radiography mode and to an intensity where no amplification of the amplifying device is saturated.

[Operation and Effect]

The radiographic apparatus of this embodiment includes description of more detail the above-mentioned radiographic apparatus provided with the radiation conversion device and the amplifying device. That is, in addition to the two elements as above, the amplification factor setting device is provided for setting an amplification factor of the amplifying device in accordance with the imaging mode. The radiation source controlling device sets output from the radiation source. Accordingly, the amplifying device and the radiation source may certainly be changed in accordance with the imaging mode set by an operator. Moreover, the radiation source controlling device sets output of single-shot radiation from the radiation source in the tomography mode to an intensity where no amplification of the amplifying device is saturated. With this configuration, the lower limit of the radiation output in the tomography mode may be defined. The lower the radiation output from the radiation source is, the higher the amplification factor of the amplifying device becomes. If the radiation output is extremely low, amplification of the amplifying device is saturated. Consequently, the contrast of the image becomes unclear. According to the foregoing configuration, tomography is conducted with radiation of a sufficient intensity so as not to introduce such saturation phenomenon. As a result, a tomographic image may be obtained suitable for diagnosis.

The above configuration also includes description in more detail the radiographic apparatus of this invention. When output of single-shot radiation from the radiation source is less in the tomography mode than in the spot radiography mode, exposure radiation to the subject may be minimized in the tomography mode. Here, two or more fluoroscopic images are superimposed to generate the tomographic image. Consequently, there is no problem even when each fluoroscopic image contains some false images.

Moreover, the above moving device moves the radiation source and the radiation detecting device synchronously in opposite directions to each other. The superimposing device superimposes a series of fluoroscopic images to generate a tomographic image. Such configuration is more desirable.

[Operation and Effect]

In the foregoing configuration, this invention is applied to the configuration that the radiation source and the radiation detecting device move synchronously in opposite directions to each other to generate the tomographic image. Superimposing the fluoroscopic images upon generation of the tomographic image may achieve cancel and removal of the false image in the fluoroscopic image.

Moreover, the foregoing moving device moves the radiation source and the radiation detecting device synchronously in an identical direction to each other. A like angle image generation device is further provided that divides a series of the fluoroscopic images into strips to generate strip-shaped images, and selects and joins the strip-shaped images having an equal angle of X-ray radiation to the radiation detecting device to obtain two or more like angle images. The superimposing device superimposes a series of the like angle images to form a tomographic image. Such configuration is more desirable.

[Operation and Effect]

In the foregoing configuration, this invention is applied to the configuration that the radiation source and the radiation detecting device move synchronously in an identical direction to generate the tomographic image. Also with such configuration, superimposing the fluoroscopic images upon formation of the tomographic image may achieve cancel and removal of the false images in the fluoroscopic image.

Moreover, the foregoing amplifying device is formed of an analog amplifier and includes an A/D converter that converts output of the amplifying device as analog data into digital data. Such configuration is more desirable.

[Operation and Effect]

According to the foregoing configuration, amplification of an electric signal is performed prior to digital conversion. Here, the electric signal prior to amplification is analog data. Consequently, the electric signal may faithfully be amplified with data in an analog format.

Moreover, an input unit is further provided for inputting operators instructions that allows variation in imaging mode. Such configuration is more desirable.

[Operation and Effect]

With the foregoing configuration, the tomography mode or the spot radiography mode may be selected through the operator's instructions. When the operator selects either of the modes, an amplification factor will be changed accordingly. Therefore, the operator may take images regardless of amplification factors.

Effect of the Invention

The radiographic apparatus according to this invention may select the spot radiography mode or the tomography mode. Moreover, the radiation detecting device provided in the radiographic apparatus according to this invention converts radiation into an electric signal, and thereafter amplifies the signal to output it to the image generation device. According to this invention, an amplification factor is higher in the tomography mode than that in the spot radiography mode. The tomographic image is obtained through superimposing two or more fluoroscopic images. In comparison of the fluoroscopic images, they differ from one another in appearance of the false image. Accordingly, superimposing the images may achieve cancel of the false image. In this way, a tomographic image finally obtained has no false image. Since the spot radiography is conducted by a low amplification factor as usual, the fluoroscopic image in the spot radiography is clear with no false image appearing therein.

BRIEF DESCRIPTION OF THE DRAWINGS

FIGS. 5 to 7 are schematic views each showing operations of a tomography mode according to Embodiment 1.

DESCRIPTION OF REFERENCES

3 . . . X-ray tube (radiation source)
4 . . . FPD (radiation detecting device)
6 . . . X-ray tube controller (radiation source control device)
7 . . . synchronously moving mechanism (moving device)
11 . . . image generation section (image generation device)
12 . . . superimposing section (superimposing device)
21 . . . console (input unit)
40 . . . conversion layer (radiation converting device)
44 . . . amplifier array (amplifying device)
45 . . . amplifier array controller (amplification factor setting device)

BEST MODE FOR CARRYING OUT THE INVENTION

Now, description will be given of the best mode in a plurality of embodiments for carrying out this invention.

Embodiment 1

Each embodiment of radiographic apparatus according to Embodiment 1 will be described hereinafter with reference to the drawings. Herein, X-rays in each embodiment correspond to radiation in Embodiment 1.

<Configuration of X-Ray Apparatus>

Figure 1:
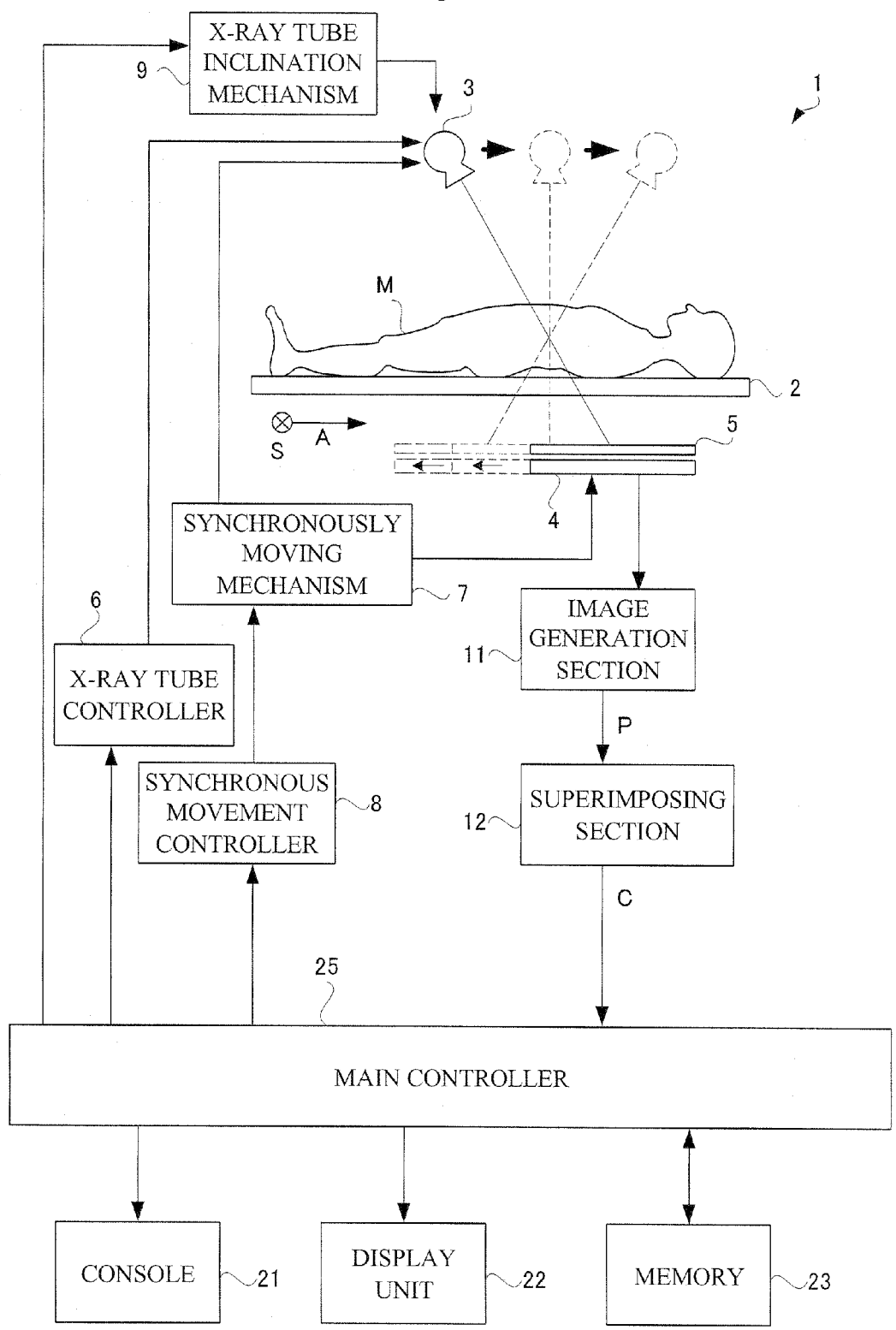
FIG. 1 is a functional block diagram showing a configuration of X-ray apparatus according to Embodiment 1.

FIG. 1 is a functional block diagram showing a configuration of radiographic apparatus according to Embodiment 1. As shown in FIG. 1, an X-ray apparatus 1 in Embodiment 1 includes a top board 2 for supporting a subject M as a target for X-ray tomography, an X-ray tube 3 disposed above the top board 2 for irradiating the subject with X-ray beams in a cone shape, a flat panel detector (hereinafter, abbreviated as FPD) 4 disposed below the top board 2 for detecting X-rays transmitting through the subject M, a synchronously moving mechanism 7 and a synchronous movement controller 8 for controlling thereof, the synchronously moving mechanism 7 moving the X-ray tube 3 and the FPD 4 synchronously in opposite directions to each other across a site of interest of the subject M while a center axis of an X-ray beam in a cone shape always conforms to a center point of the FPD 4, an X-ray grid 5 provided as to cover an X-ray detecting surface of the FPD 4 detecting X-rays of the FPD 4 for absorbing scattered X-rays. Thus, the X-ray tube 3, the top board 2, and the FPD 4 are arranged in this order in a vertical direction. The X-ray apparatus 1 corresponds to the radiographic apparatus in this invention. The X-ray tube 3 corresponds to the radiation source in this invention. Moreover, the FPD 4 corresponds to the radiation detecting device in this invention. The synchronously moving mechanism 7 corresponds to the moving device in this invention.

The X-ray tube 3 is configured to repeat irradiation of the subject M with the cone-shaped and pulsed X-ray beams under control by the X-ray tube controller 6. The X-ray tube 3 has a collimator attached thereto for collimating the X-ray beam into a shape of a pyramid cone. This X-ray tube 3 and the FPD 4 constitute imaging systems 3 and 4 for acquiring X-ray fluoroscopic images. The X-ray tube controller 6 corresponds to the radiation source control device in this invention.

The X-ray apparatus 1 according to Embodiment 1 further includes a main controller 25 for performing overall control of the controllers 6 and 8, and a display unit 22 for displaying an X-ray tomographic image. The main controller 25 has a CPU and, by executing various programs; constructs the controllers 6 and 8, an image generation section 11, and a superimposing section 12, mentioned later. The superimposing section 12 corresponds to the superimposing device in this invention. The image generation section 11 corresponds to the image generation device in this invention.

The operator inputs instructions through the console 21. Accordingly, the operator may select either spot radiography or tomography, and instruct starting imaging. The console 21 corresponds to the input device in this invention.

The synchronously moving mechanism 7 moves the X-ray tube 3 and the FPD 4 synchronously. This synchronously moving mechanism 7, under control of the synchronous movement controller 8, moves the X-ray tube 3 straight along a linear track parallel to the direction of the body axis A of the subject M. Moreover, the cone-shaped X-ray beam emitted from the X-ray tube 3 during examination is always emitted toward the site of interest of the subject M. This X-ray emission angle is changed, for example, from an initial angle of −20° to a final angle of 20° by changing an angle of the X-ray tube 3. An X-ray tube inclination mechanism 9 performs such changes of the X-ray emission angle. The synchronous movement controller 8 controls the synchronously moving mechanism 7 and the X-ray tube inclination mechanism 9 synchronously. The body axis A corresponds to the movement direction in this invention.

The synchronously moving mechanism 7 moves the FPD 4, disposed below the top board 2, straight along the direction of the body axis A of the subject M, synchronously with straight movement of the X-ray tube 3 noted above. The moving direction of the FPD 4 is opposite to the moving direction of the X-ray tube 3. That is, the cone-shaped X-ray beam with the emission source position and the direction of emission changing through movement of the X-ray tube 3 is always received on the entire X-ray detecting plane of the FPD 4. Thus, for one examination, the FPD 4 acquires 74 fluoroscopic images P, for example, while synchronously moving with the X-ray tube 3 in opposite directions. Specifically, the imaging systems 3 and 4 move, as opposed to each other, from an initial position shown in solid lines through a position shown in dashed lines toward a position shown in chain lines. That is, a plurality of X-ray fluoroscopic images are acquired while changing positions of the X-ray tube 3 and the FPD 4. Since the cone-shaped X-ray beam is always received on the entire X-ray detecting plane of the FPD 4, the center of the cone-shaped X-ray beam always passes through the center point of the FPD 4 during imaging. During radiography, the center of the FPD 4 moves straight, and this movement is opposite to the direction of movement of the X-ray tube 3. In other words, the X-ray tube 3 and the FPD 4 may move synchronously and adversely to each other along the body axis direction A.

Figure 2:
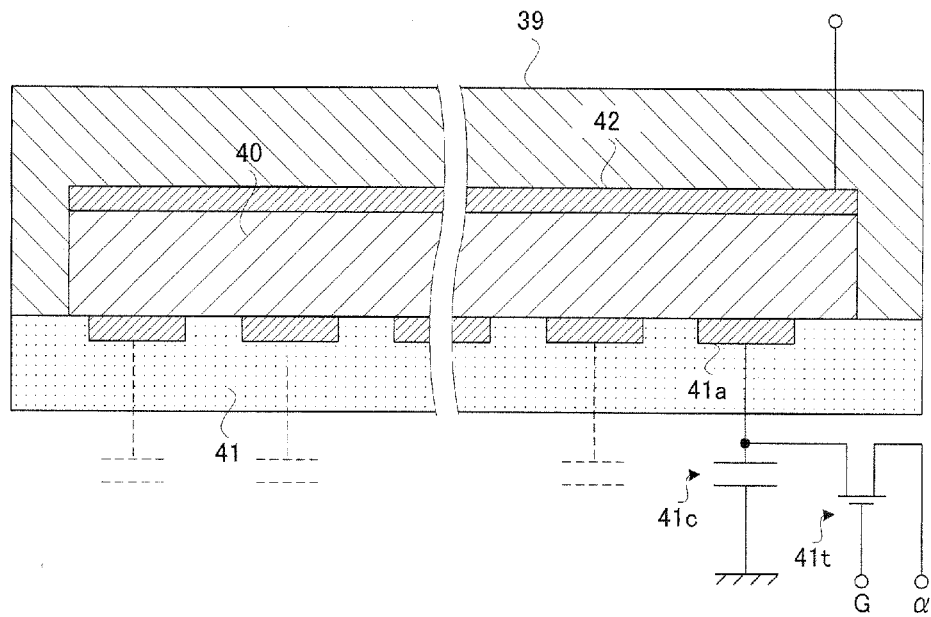
FIG. 2 is a sectional view showing a configuration of an FPD according to Embodiment 1.
Figure 3:
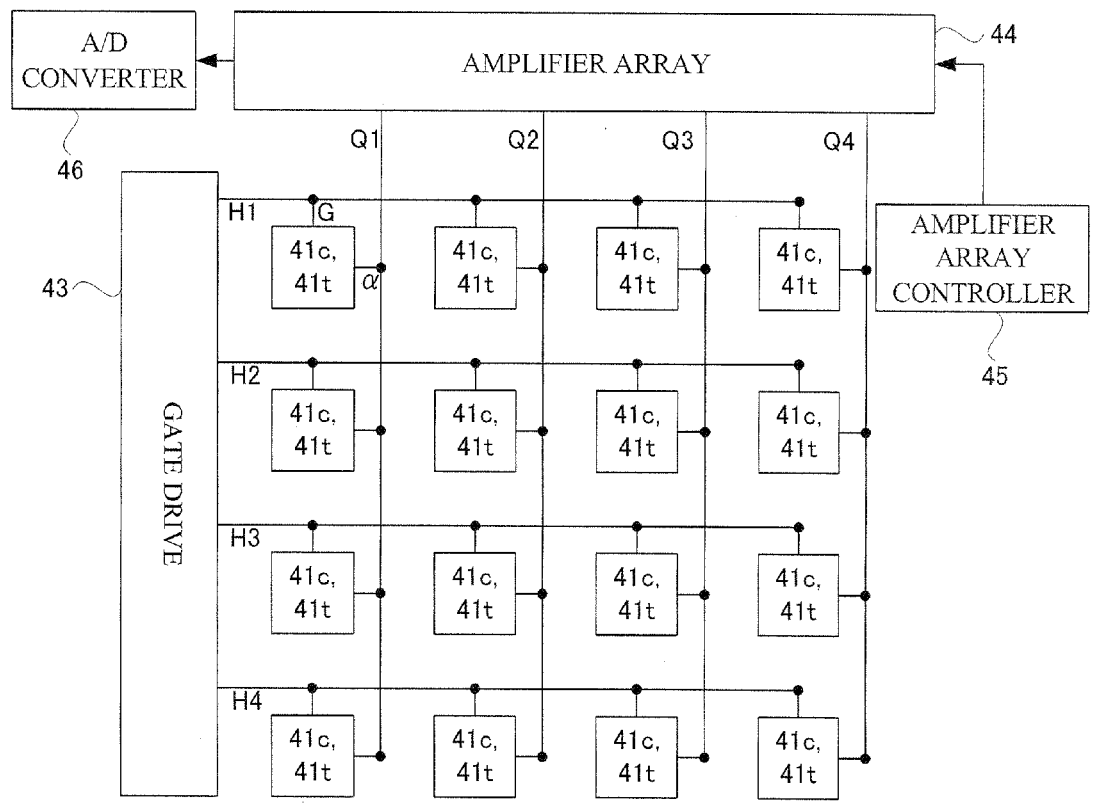
FIG. 3 is a schematic view showing a configuration of the FPD according to Embodiment 1.

Description will be given of a configuration of the FPD 4. As shown in FIG. 2, the FPD 4 includes a conversion layer 40 composed of amorphous selenium, an active matrix substrate 41 laminated on the conversion layer 40, and a plane electrode 42 for placing the conversion layer 40 on a given electric field. Collection electrodes 41a for carrier collection are provided in the active matrix substrate 41 so as to contact the conversion layer 40. The collection electrodes 41a are arranged in a matrix over a plane of the active matrix substrate 41. Each of the collection electrodes 41a is provided with a capacitor 41c for accumulating electric charges. Each of the capacitors 41c is provided with a transistor 41t for controlling extraction of electric charges. Accordingly, the capacitor 41c and the transistor 41t are arranged two-dimensionally as shown in FIG. 3. Here, the plane electrode 42 is covered with an insulating layer 39. The conversion layer 40 corresponds to the radiation conversion device in this invention. One capacitor 41c and one transistor 41t connected thereto form a single X-ray detecting element.

The transistors 41t arranged two-dimensionally are connected to wires extending vertically and horizontally in a lattice shape. Specifically, read-out electrodes a of the transistors 41t arranged in the vertical direction in FIG. 3 are each connected to any of common amplifying electrodes Q1 to Q4. Gates G of the transistors 41t arranged in the horizontal direction in FIG. 2 are each connected to any of common gate control electrodes H1 to H4. The gate control electrodes H1 to H4 are connected to a gate drive 43, and the amplifying electrodes Q1 to Q4 are connected to an amplifying array 44. The amplifying array 44 is formed of analog amplifiers arranged in an array. The amplifying array 44 corresponds to the amplifying device in this invention.

Description will be given of a configuration for reading out electric charges to each capacitor 41c. Here, it is assumed that electric charges are accumulated in each of the capacitors 41c in FIG. 3. The gate drive 43 turns on the transistors 41t simultaneously through the gate control electrode H1. The four transistors 41t turned on and located in the horizontal direction transmit electric charges (original signals) to the amplifier array 44 through the amplifying electrodes Q1 to Q4. The original signal is analog data, and corresponds to the electric signal in this invention.

Next, the gate drive 43 turns on the transistors 41t simultaneously through the gate control electrode H2. In this way, the gate drive 43 turns on the gate control electrodes H1 to H4 in turn. The transistors 41t arranged in the same lines are turned on each time. In this way, the FPD 4 reads out electric charges accumulated in each of the capacitor 41c for every line.

The amplifier array 44 has an amplifier in each of the amplifying electrodes Q1 to Q4 for amplifying signals. The original signals inputted from the amplifying electrodes Q1 to Q4 into the amplifier array 44 are amplified by a given amplification factor. The amplified signal as analog data outputted from the amplifier array 44 is converted into digital by an A/D converter 46, and thereafter is outputted to the image generation section 11. The amplified signals are each converted into a pixel value to be arranged two-dimensionally, whereby an image is generated. The A/D converter 46 corresponds to the A/D conversion device in this invention. The A/D converter 46 is provided for every amplifier.

The amplifier array 44 amplifies the original signal based on an analog gain (amplification factor) outputted from an amplifier array controller 45. When the amplifier array controller 45 outputs a value "3" as an analog gain, the amplifier array 44 amplifies the original signal outputted from transistor 41t three times to output amplified signals. The amplifier array controller 45 corresponds to the amplification factor setting device in this invention.

Figure 4:
FIG. 4 is a schematic view showing a table according to Embodiment 1.

A memory unit memorizes table T having an analog gain and a parameter with respect to control of the X-ray tube 3 correlated with each other (see FIG. 4.) Each parameter for spot radiography with respect to control of X-ray tube 3 is correlated with an analog gain for spot radiography. Moreover, each parameter for tomography with respect to control of the X-ray tube 3 is correlated with an analog gain for tomography. The analog gain for tomography has a value higher than that for spot radiography. Each parameter with respect to control of the X-ray tube 3 is specified so that lower X-rays are outputted in tomography rather than in spot radiography. Specifically, the parameter is a tube current, a tube voltage, and a pulse width (irradiation time per pulse of X-ray beams) of the X-ray tube 3. With the parameter configured as above, when the single-shot X-ray pulse in tomography impinges upon a subject, exposure is suppressed to be lower than that in spot radiography. In tomography, the subject is to be irradiated with X-ray pulses 74 times.

A radiation beam has lower radiation intensity per single shot in tomography than in spot radiography. Such control of outputting a radiation beam may be achieved through adjustment of a pulse width of a radiation beam, or through adjustment of a tube current and a tube voltage of a radiation beam. Alternatively, the pulse width, the tube current, and the tube voltage may all be adjusted.

Figure 5:
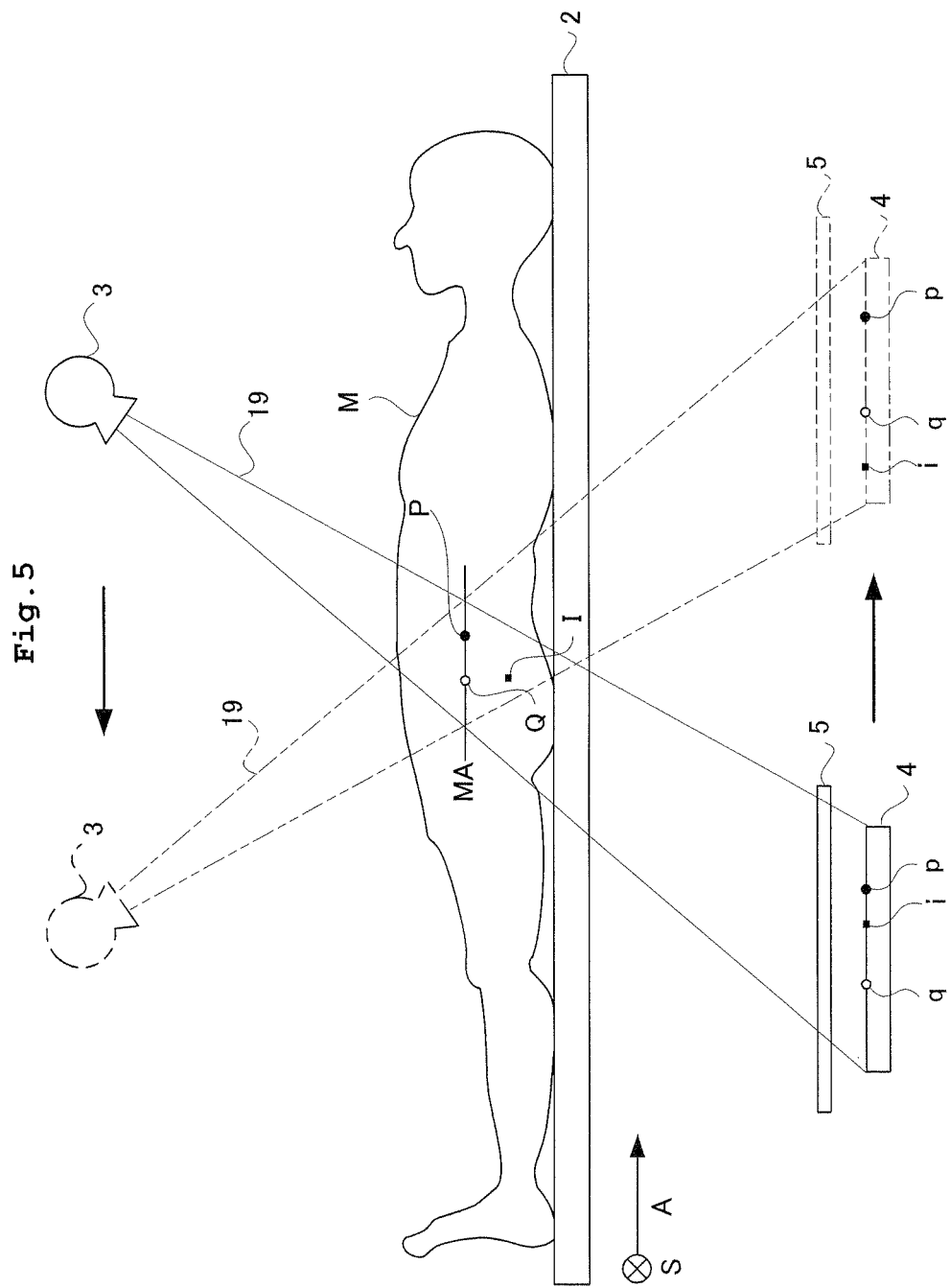

Next, description will be given of the principle of acquiring a tomographic image with the tomography X-ray apparatus 1 according to Embodiment 1. FIG. 5 is a view showing a method of acquiring a tomographic image with the X-ray apparatus according to Embodiment 1. To describe the principle taking a reference sectional plane MA parallel to the top board 2 (horizontal relative to the vertical direction) as shown in FIG. 5, for example, the fluoroscopic image generation section 11 generates a series of fluoroscopic images of the subject while the FPD 4 moves synchronously with and in an opposite direction to the X-ray tube 3 according to the direction of emission of the cone-shaped X-ray beam 19, so that points P and Q located in the reference sectional plane MA may always be projected to fixed points p and q, respectively, on the X-ray detecting plane of the FPD 4. The projected image of the subject falls on a series of the subject images Pm while varying in position. Then, the superimposing section 12 superimposes the series of the subject images Pm, thereby joining images located in the reference sectional plane MA (e.g. fixed points p and q), and resulting in an X-ray sectional image. On the other hand, point I not located in the reference sectional plane MA appears in the series of the subject images as points i, while varying in projected position in the FPD 4. As distinct from fixed points p and q, such points i become blurred, instead of forming an image, at the step of superimposing the X-ray fluoroscopic images in the superimposing section 12. An X-ray sectional image showing only the images located in the reference sectional plane MA of the subject M may be obtained through superimposing the series of the subject images in this way. Thus, when the X-ray fluoroscopic images are simply superimposed, an X-ray sectional image on the reference sectional plane MA may be obtained. Here, a position of the reference sectional plane MA in the vertical direction corresponds to the reference sectional position in this invention.

Further, a similar sectional image may be obtained from any selected section parallel to the reference sectional plane MA, by changing settings of the superimposing unit 12. Although the projected position of point i described above moves on the FPD 4 during imaging, a speed of this movement increases as a distance increases between point I before projection and the reference sectional plane MA. Thus, the series of subject images obtained in this way is superimposed while being shifted in the body axis direction A at given pitches, whereby an X-ray sectional image at a section parallel to the reference sectional plane MA may be obtained. The superimposing section 12 superimposes the series of the subject images in this way. The method of obtaining a sectional image in this way is called a filter back projection.

<Operation of X-Ray Apparatus>

Next, description will be given of operations of X-ray apparatus according to Embodiment 1. For effectively illustrating the characteristic in the configuration of Embodiment 1, spot radiography is firstly conducted to a subject, and then tomography is conducted. First, a subject is placed on a top board 2. When an operator instructs via the console 21 movement of the X-ray tube 3 and the FPD 4, the X-ray tube 3 and the FPD 4 each move to a position identical in body axis direction of the subject M. A portion of the subject M between the X-ray tube 3 and the FPD 4 is a site of interest of the subject M fluoroscoped through spot radiography.

When the operator instructs start of spot radiography through the console 21, the X-ray apparatus 1 goes into a spot radiography mode. Then, the X-ray tube controller 6 acquires a parameter for spot radiography from the memory 23. The amplifier array controller 45 acquires an analog gain for spot radiography from the memory 23. Accordingly, the image generation section 11 generates a fluoroscopic image P with a high contrast using radiation of relatively high intensity, and a display unit 22 displays it. Thus, the X-ray tube controller 6 sets output of the X-ray tube 3 depending on a selection mode selected upon imaging, thereby controlling the X-ray tube 3. Moreover, the amplifier array controller 45 sets an amplification factor of the amplifier array 44 depending on the imaging mode selected upon imaging. In other words, when the imaging mode is changed in the X-ray apparatus 1, output of the X-ray tube 3 and an amplification factor of the amplifier array 44 are changed to be suitable for the imaging mode.

Subsequently, when the operator provides instructions on starting tomography of the subject through the console 21, the X-ray apparatus 1 switches to tomography mode. Then, the X-ray tube controller 6 acquires a parameter for tomography from the memory 23. The amplifier array controller 45 acquires an analog gain for tomography from the memory 23. Conventionally, radiation of relatively low intensity is adopted, and thus a fluoroscopic image with a low contrast should be obtained. However, an analog gain that the amplifier array controller 45 acquires is higher than that upon spot radiography. Accordingly, original signals outputted from the transistors 41t are amplified by a high amplification factor, and a fluoroscopic image with a high contrast is generated in the image generation section 11. As shown in table T in FIG. 4, an analog gain in the tomography mode is 10 times. The X-ray tube 3 and the FPD 4 move in opposite directions to each other along the body axis A of the subject to obtain 74 fluoroscopic images P1 to P74.

Figure 7:

A noise component (false image) superimposed on the original signals appears in the fluoroscopic image P amplified by a high amplification factor. Specifically, as shown in FIG. 6, a granular false image appears in each fluoroscopic image P. Even when this is under spot radiography, the granular false image will not be removed. On the other hand, in tomography, a false image is to be removed during superimposing of the fluoroscopic images P. The fluoroscopic images P differ from one another in pattern of the granular false image because the false image superimposed on the original signals varies temporally. Such granular false image is cancelled when the superimposing section 12 superimposes the fluoroscopic images P. Accordingly, no influence of the noise appears in the tomographic image C as shown in FIG. 7. In this way, tomographic image C superior to visibility is displayed on the display unit 22. Here, a region illustrated by shading in FIG. 6 is a fluoroscoped image of the subject appearing in the fluoroscopic image P.

Moreover, the X-ray tube controller 6 controls output of single shot X-rays of the X-ray tube 3 in the tomography mode to an intensity where no amplification of the amplifier array 44 is saturated. The lower the output of X-rays is, the lower the level of the original signal from the X-ray detecting element becomes. In order to use the lower level of the original signal for generation of a tomographic image, it is necessary to amplify the original signal by a higher amplification factor. However, the amplification factor of the amplifier array 44 has its limitation. That is, when the amplifier array 44 is amplified by a higher amplification factor, amplification thereof is to be saturated. Accordingly, the amplifier array 44 outputs the same output data as the A/D converter 46 regardless of level of the original signal from the detecting element. That is, the fluoroscopy image of the subject M shown by level of the original signal outputted from the X-ray detecting elements is to be removed by the amplifier array 44. Such saturation phenomena of the amplifier array 44 may avoid generation of the fluoroscopic image C.

In view of the state of the art mentioned above, Embodiment 1 has a configuration that imaging is conducted with sufficient high output of X-rays in the tomography mode. Accordingly, no saturation phenomenon of the amplifier array 44 occurs. Consequently, a fluoroscoped image of the subject M shown by level of the original signals outputted from the detecting elements is not removed by the amplifier array 44, but certainly sent to the generation section 11.

Embodiment 2

Figure 8:
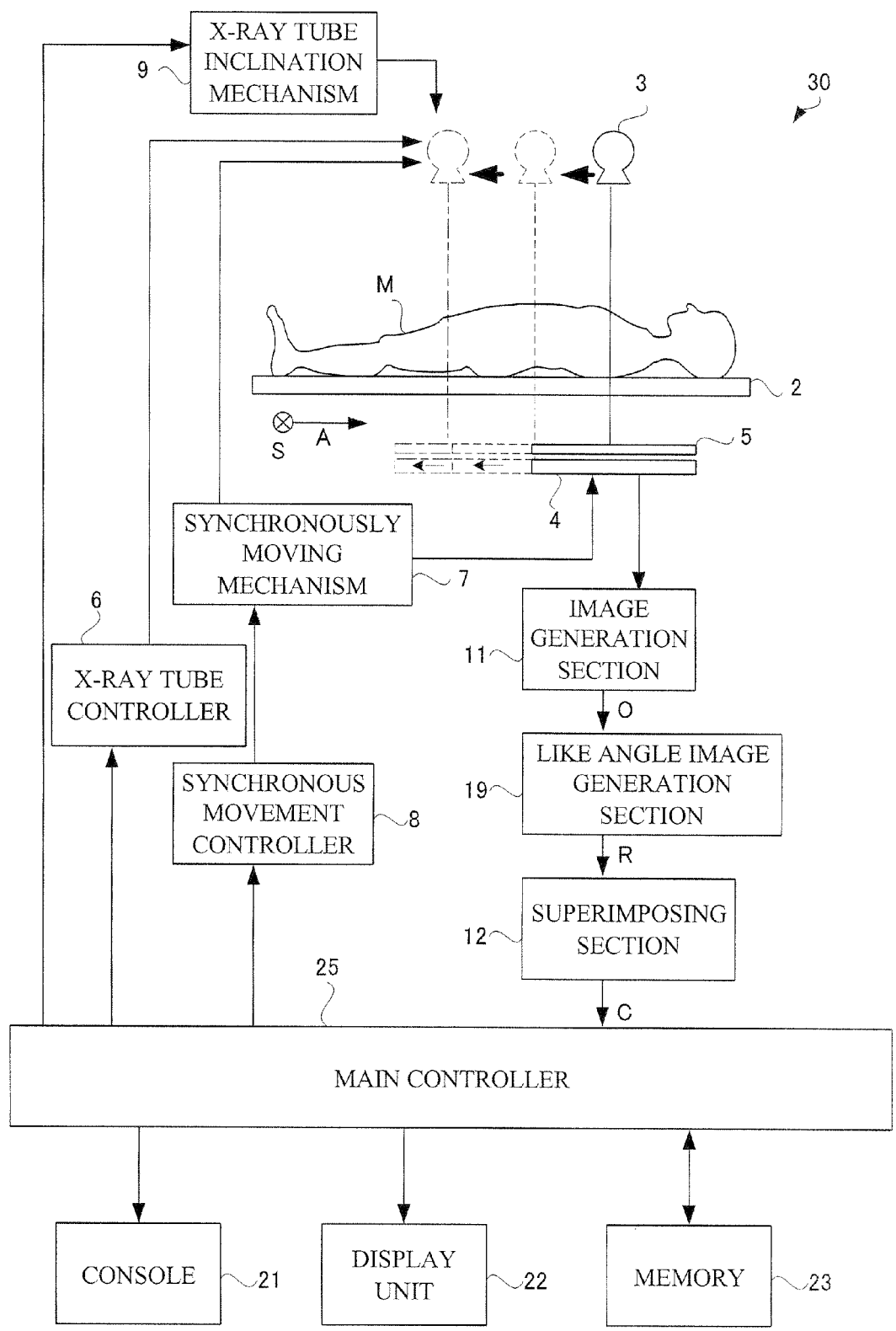
FIG. 8 is a functional block diagram showing a configuration of X-ray apparatus according to Embodiment 2.

Next, X-ray apparatus 30 according to Embodiment 2 will be described. FIG. 8 is a functional block diagram of tomographic X-ray apparatus according to Embodiment 2. As shown in FIG. 8, the X-ray apparatus according to Embodiment 2 is similar to the configuration described in Embodiment 1. Therefore, description of like components will be omitted as appropriate. The configuration of Embodiment 2 is different from that of Embodiment 1 in the mode of movement of the X-ray tube 3 and FPD 4 and the mode of image processing of X-ray fluoroscopic images. The FPD 4 has the same configuration as that in Embodiment 1, and thus description thereof is to be omitted.

The synchronously moving mechanism 7 moves the FPD 4 disposed below the top board 2 straight along the direction of the body axis A of a subject M synchronously with straight movement of the X-ray tube 3 described above. The FPD 4 has the same moving direction as the X-ray tube 3. That is, the cone-shaped X-ray beam with the emission source position and the direction of emission changing through movement of the X-ray tube 3 is always received on the entire X-ray detecting plane of the FPD 4. Thus, for one examination, the FPD 4 acquires 74 X-ray fluoroscopic images, for example, while synchronously moving with the X-ray tube 3 in the same direction. Specifically, the X-ray tube 3 and FPD 4 move in the same direction through a position shown in dashed lines to a position shown in chain lines.

The cone-shaped X-ray beam emitted from the X-ray tube 3 during examination is always directed toward a site of interest of the subject M. This X-ray emission angle is constantly at 0° during acquisition of a series of X-ray fluoroscopic images.

The X-ray apparatus 30 further includes a like angle image generation section 19 between the image generation section 11 and the superimposing section 12 for generating like angle images described hereinafter.

Next, the principle of acquiring a tomographic image with the X-ray apparatus 30 according to Embodiment 2 will be described. The 74 X-ray fluoroscopic images acquired serially are generated by the image generation section 11, and thereafter outputted to the like angle image generation section 19 where, for example, fifty like angle images are generated. The fifty like angle images may be superimposed by the superimposing section 12, to acquire a desired X-ray tomographic image.

Operation of the like angle image generation section 19 will be described. The like angle image generation section 19 first divides each obtained X-ray fluoroscopic image along a direction perpendicular to the synchronous moving direction of the X-ray tube 3 and the FPD 4 to acquire fifty strip-shaped images, for example. From 3,700 (=74×50) strip-shaped images obtained from the series of X-ray fluoroscopic images, the like angle image generation section 19 selects and joins strip-shaped images having an equal angle of X-ray irradiation, to acquire a like angle image. Since each of the X-ray fluoroscopic images is divided into fifty parts, fifty like angle images are to be acquired. Although the X-ray beam according to this invention is cone-shaped, the above process enables accommodation of a reconstructing method in tomographic X-ray apparatus using a well-known elongate X-ray beam.

Figure 9:
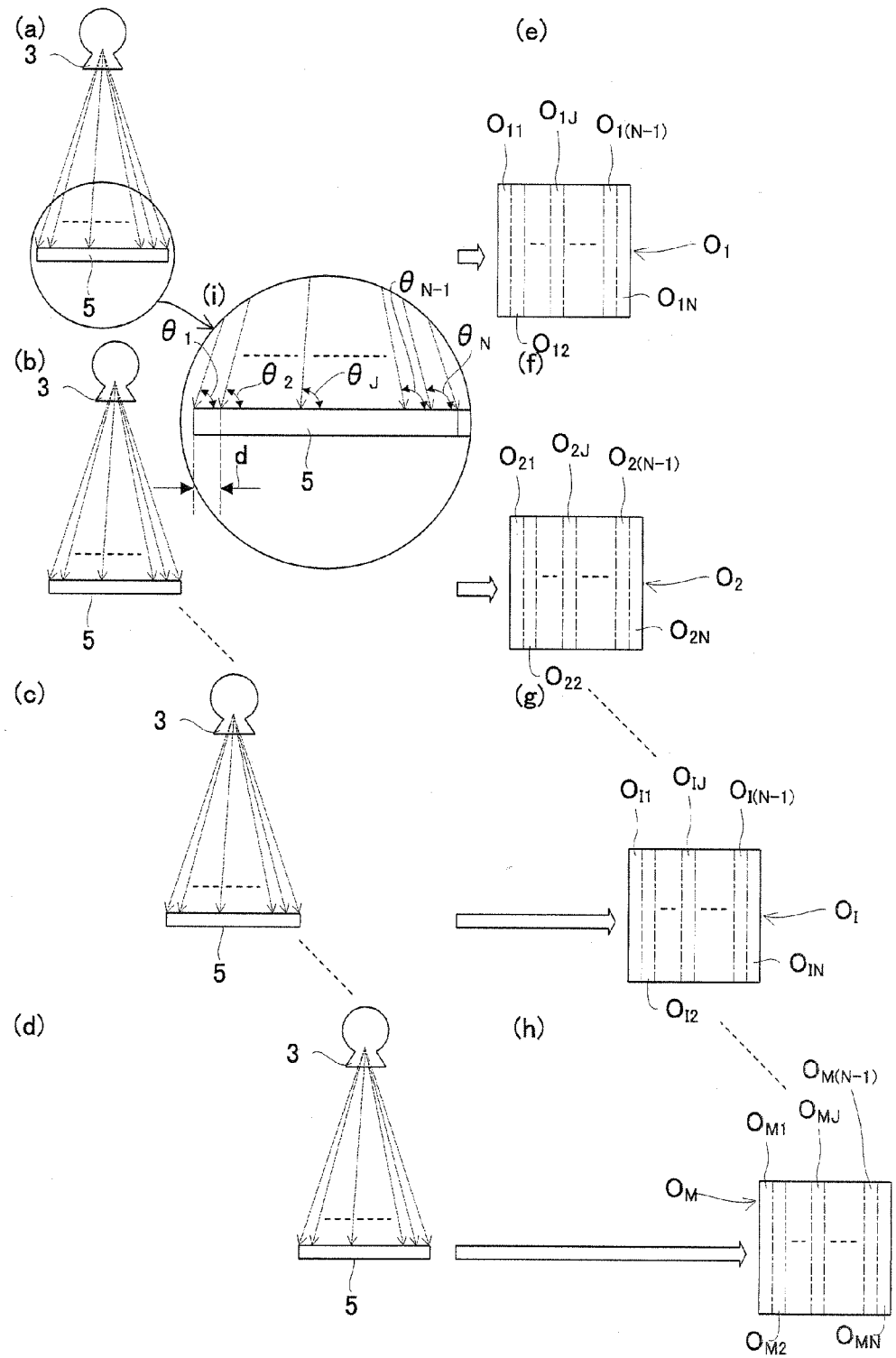
FIGS. 9 to 12 are schematic views each showing operations of a tomography mode according to Embodiment 2.
Figure 10:
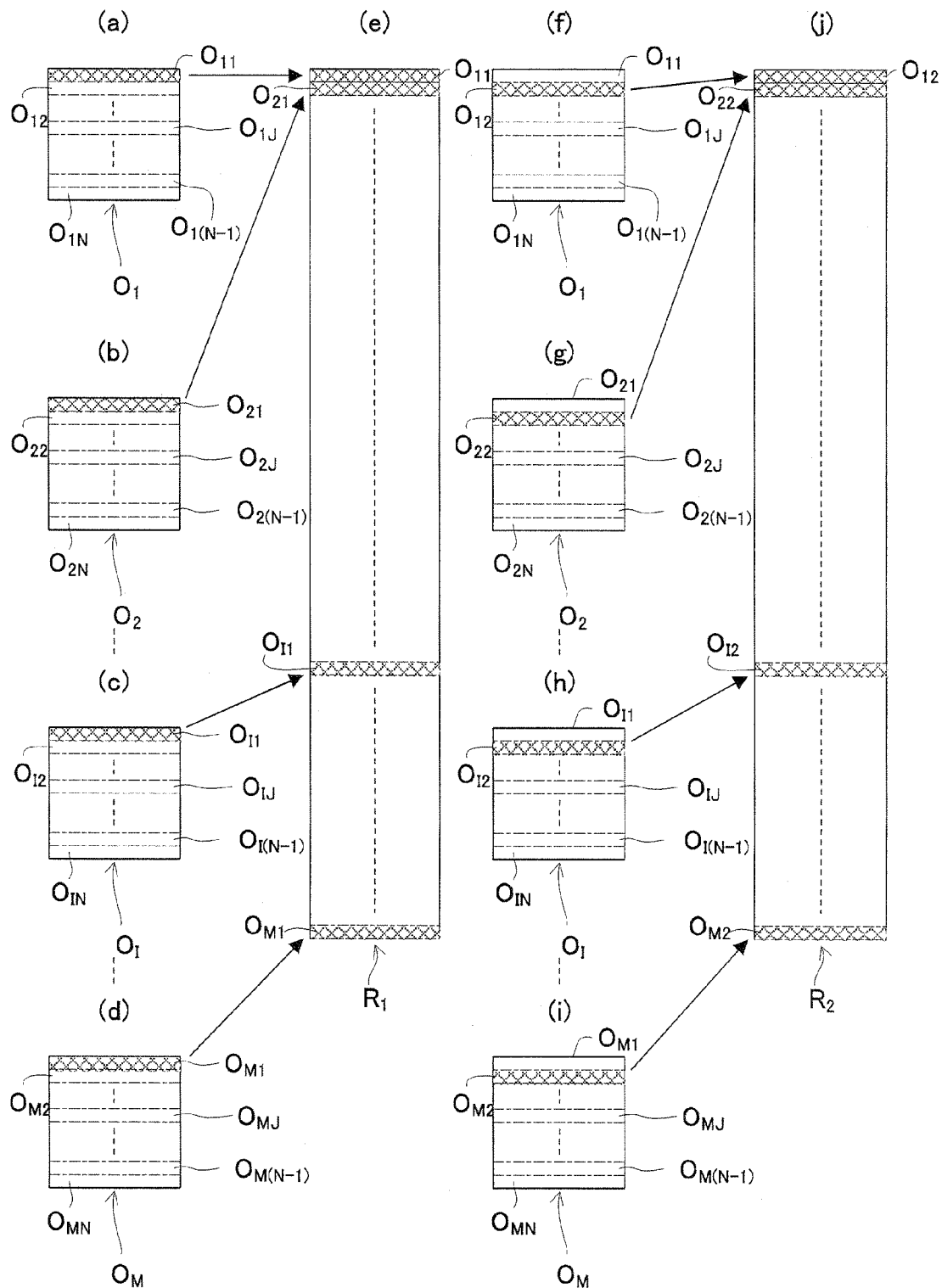
Figure 11:
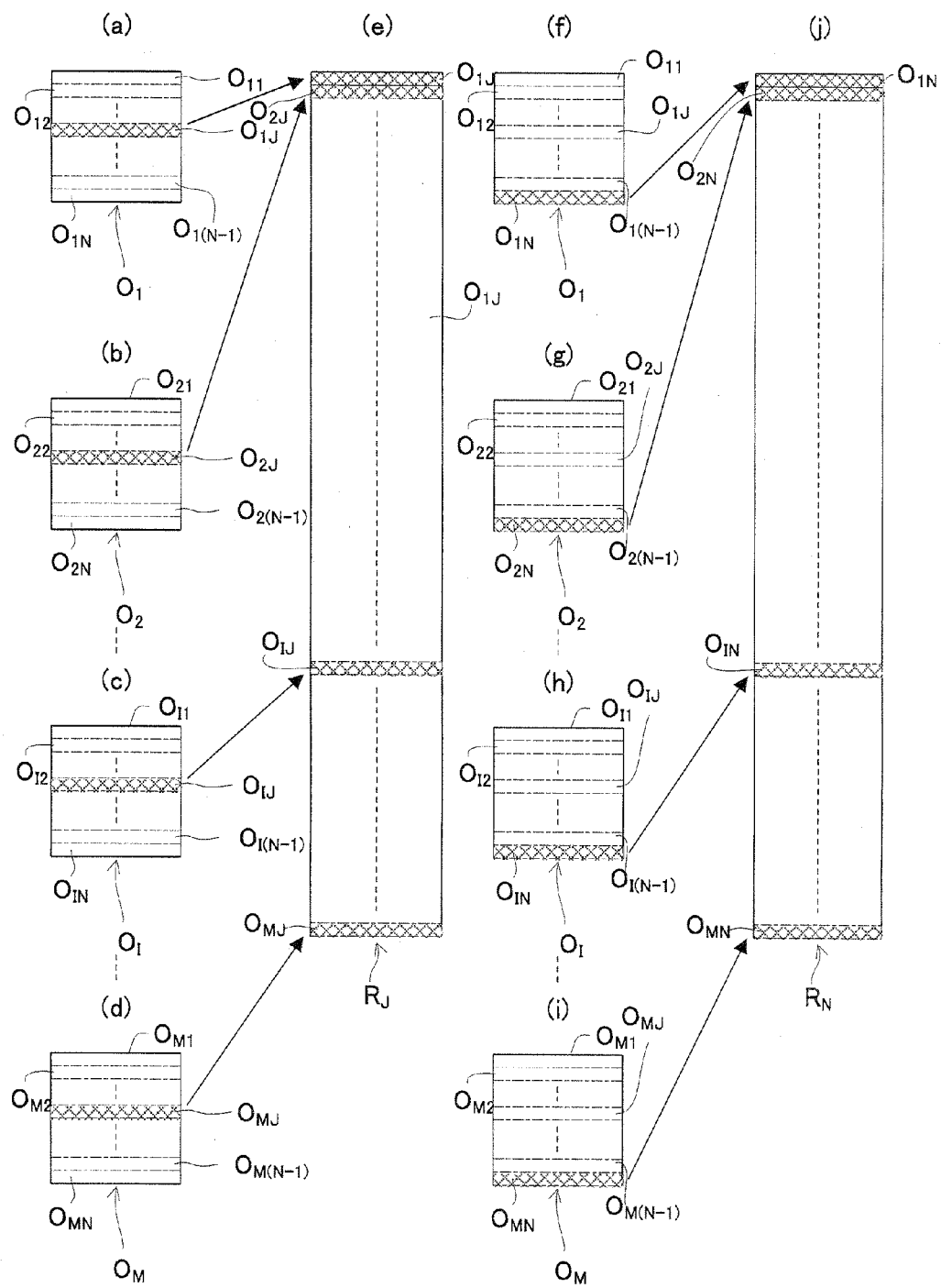

The image processing performed with the like angle image generation section 19 will be described in more detail. FIGS. 9 through 11 are schematic views each illustrating image processing with the like angle image generation section for acquiring an X-ray tomographic image according to Embodiment 2. Preliminary to the description, it is assumed that, as the X-ray tube 3 moves every pitch d as shown in FIG. 9(a) to FIG. 9(d), X-ray fluoroscopic images are taken by the detecting plane of the FPD 4, which are referred to as $O_1, O_2, \ldots, O_I, \ldots, O_M$ as shown in FIG. 9(e) to FIG. 9(h) ($1 \leq I \leq M$). While the X-ray tube 3 moves every pitch d, the X-ray tube 3 emits X-rays intermittently. That is, whenever the X-ray tube 3 moves every pitch d, it gives a pulsed irradiation of X-rays. The FPD 4 moves synchronously with the X-ray tube 3.

Specifically, when the X-ray tube 3 emits X-rays first in a position shown in FIG. 9(a), the X-ray tube 3 emits X-rays next in a position shifted by one pitch d, shown in FIG. 9(b). The FPD 4 detects X-rays as in FIG. 9(a), whereby an X-ray fluoroscopic image $O_1$ (see FIG. 9(e)) is acquired. The FPD 4 detects X-rays as in FIG. 9(b), whereby an X-ray fluoroscopic image $O_2$ (see FIG. 9(f)) is acquired. Subsequently, the X-ray tube 3 emits X-rays for an (I−1)th time in a position shown in FIG. 9(c) while similarly moving every pitch d, and the FPD 4 detects the X-rays in FIG. 9(c), whereby an X-ray fluoroscopic image $O_I$ (see FIG. 9(g)) may be obtained. Finally, X-rays are emitted for an (M−1)th time in a position shown in FIG. 9(d), and the FPD 4 detects the X-rays in FIG. 9(d), whereby an X-ray fluoroscopic image $O_M$ (see FIG. 9(h)) may be obtained. In Embodiment 2, an imaging start position in FIG. 9(a) is adjacent the feet of the subject M, and an imaging end position in FIG. 9(d) is adjacent the head of the subject M. As the X-ray tube 3 and the FPD 4 move as in FIG. 9(a) to FIG. 9(d), movement is made in order along the direction of the body axis A of the subject M.

With the X-ray tube 3 moving every pitch d, each of the X-ray fluoroscopic images $O_1, O_2, \ldots, O_I, \ldots, O_M$ may be separated according to pitches d. Specifically, as shown in an enlarged view in FIG. 9(i), projection angles formed between the radiation axis extending from the X-ray tube 3 to the FPD 4 and the body axis of the subject M are set to $\theta_1, \theta_2, \ldots, \theta_J, \ldots, \theta_{N-1}$ and $\theta_N$ for the respective pitches d ($1 \leq J \leq N$). Then, the images separated into the pitches d are in agreement with the strip-shaped images divided into like projection angles $\theta_1, \theta_2, \ldots, \theta_J, \ldots, \theta_{N-1}$ and $\theta_N$, respectively.

The X-ray fluoroscopic image $O_1$ is separated into $O_{11}, O_{12}, \ldots, O_{1J}, \ldots, O_{1(N-1)}$ and $O_{1N}$ according to the pitches d as shown in FIG. 9(e). The separated strip-shaped image $O_{11}$ is an image derived from irradiation at projection angle $\theta_1$. The separated strip-shaped image $O_{12}$ is an image derived from irradiation at projection angle $\theta_2$. Subsequently, the similarly separated strip-shaped image $O_{1J}$ is an image derived from irradiation at projection angle $\theta_J$. The finally separated strip-shaped image $O_{1N}$ is an image derived from irradiation at projection angle $\theta_N$.

Similarly, the X-ray fluoroscopic image $O_2$ is separated into $O_{21}, O_{22}, \ldots, O_{2J}, \ldots, O_{2(N-1)}$ and $O_{2N}$ according to the pitches d as shown in FIG. 9(f). The separated strip-shaped image $O_{21}$ is an image derived from irradiation at projection angle $\theta_1$.

The separated strip-shaped image $O_{22}$ is an image derived from irradiation at projection angle $\theta_2$. Subsequently, the similarly separated strip-shaped image $O_{2J}$ is an image derived from irradiation at projection angle $\theta_J$. The finally separated strip-shaped image $O_{2N}$ is an image derived from irradiation at projection angle $\theta_N$.

For the (I−1)th time, the X-ray fluoroscopic image $O_1$ is separated into $O_{11}, O_{12}, \ldots, O_{1J}, \ldots, O_{1(N-1)}$ and $O_{1N}$ according to the pitches d as shown in FIG. 9(g). The separated strip-shaped image $O_{11}$ is an image derived from irradiation at projection angle $\theta_1$. The separated strip-shaped image $O_{12}$ is an image derived from irradiation at projection angle $\theta_2$. Subsequently, the similarly separated strip-shaped image $O_{1J}$ is an image derived from irradiation at projection angle $\theta_J$. The finally separated strip-shaped image $O_{1N}$ is an image derived from irradiation at projection angle $\theta_N$.

Finally, for the (M−1)th time, the X-ray fluoroscopic image $O_M$ is separated into $O_{M1}, O_{M2}, \ldots, O_{MJ}, \ldots, O_{M(N-1)}$ and $O_{MN}$ according to the pitches d as shown in FIG. 9(h). The separated strip-shaped image $O_{M1}$ is an image derived from irradiation at projection angle $\theta_1$. The separated strip-shaped image $O_{M2}$ is an image derived from irradiation at projection angle $\theta_2$. Subsequently, the similarly separated strip-shaped image $O_{MJ}$ is an image derived from irradiation at projection angle $\theta_J$. The finally separated strip-shaped image $O_{MN}$ is an image derived from irradiation at projection angle $\theta_N$.

The separated images as described above are combined according to the like projection angles $\theta_1, \theta_2, \ldots, \theta_J, \ldots \theta_{N-1}$ and $\theta_N$, respectively, as shown in FIGS. 10 and 11. As noted above, each of the X-ray fluoroscopic images $O_1, O_2, \ldots, O_I, \ldots, O_M$ has images separated according to pitches d (that is, divided into projection angles $\theta_1, \theta_2, \ldots, \theta_{N-1}$ and $\theta_N$) as shown in FIGS. 10(a) to 10(d), FIGS. 10(f) to 10(i), FIGS. 11(a) to 11(d), and FIGS. 11(f) to 11(i).

In a projection angle of $\theta_1$, for example, the strip-shaped image $O_{11}$ in the X-ray fluoroscopic image $O_1$ shown in FIG. 10(a), the strip-shaped image $O_{21}$ in the X-ray fluoroscopic image $O_2$ shown in FIG. 10(b), the strip-shaped image $O_{I1}$ in the X-ray fluoroscopic image $O_I$ shown in FIG. 10(c), and the strip-shaped image $O_{M1}$ in the X-ray fluoroscopic image $O_M$ shown in FIG. 10(d) are combined to obtain a like angle image $R_1$ for projection angle $\theta_1$ as shown in FIG. 10(e).

Similarly, in a projection angle of $\theta_2$, the strip-shaped image $O_{12}$ in the X-ray fluoroscopic image $O_1$ shown in FIG. 10(f), the strip-shaped image $O_{22}$ in the X-ray fluoroscopic image $O_2$ shown in FIG. 10(g), the strip-shaped image $O_{I2}$ in the X-ray fluoroscopic image $O_I$ shown in FIG. 10(h), and the strip-shaped image $O_{M2}$ in the X-ray fluoroscopic image $O_M$ shown in FIG. 10(i) are combined to obtain a like angle image $R_2$ for projection angle $\theta_2$ as shown in FIG. 10(j).

In a projection angle of $\theta_J$, for the (J−1)th time, the strip-shaped image $O_{1J}$ in the X-ray fluoroscopic image $O_1$ shown in FIG. 11(a), the strip-shaped image $O_{2J}$ in the X-ray fluoroscopic image $O_2$ shown in FIG. 11(b), the strip-shaped image $O_{IJ}$ in the X-ray fluoroscopic image $O_1$ shown in FIG. 11(c), and the strip-shaped image $O_{MJ}$ in the X-ray fluoroscopic image $O_M$ shown in FIG. 11(d) are combined to obtain a like angle image $R_J$ for projection angle $\theta_3$ as shown in FIG. 11(e).

Finally, in a projection angle of $\theta_N$, for the (N−1)th time, the strip-shaped image $O_{1N}$ in the X-ray fluoroscopic image $O_1$ shown in FIG. 11(f), the strip-shaped image $O_{2N}$ in the X-ray fluoroscopic image $O_2$ shown in FIG. 11(g), the strip-shaped image $O_{IN}$ in the X-ray fluoroscopic image $O_1$ shown in FIG. 11(h), and the strip-shaped image $O_{MN}$ in the X-ray fluoroscopic image $O_M$ shown in FIG. 11(i) are combined to obtain a like angle image $R_N$ for projection angle $\theta_N$ as shown in FIG. 11(j).

To summarize the above, the like angle image generation section 19 combines the images separated according to the like projection angles $\theta_1, \theta_2, \ldots, \theta_J, \ldots, \theta_{N-1}$ and $\theta_N$, to obtain like angle images $R_1, R_2, \ldots,$ and $R_N$ for projection angles $\theta_1, \theta_2, \ldots, \theta_J, \ldots, \theta_{N-1}$ and $\theta_N$, as shown in FIGS. 10(e), 10(j), 11(e), and 11(j).

The superimposing section 12 obtains a tomographic image by performing a reconstruction process based on the combined like angle images $R_1, R_2, \ldots, R_J, \ldots,$ and $R_N$. The reconstruction process may be performed using the well-known filtered back projection (FBP).

<Operation of X-Ray Apparatus>

Next, description will be given of operations of X-ray apparatus according to Embodiment 2. For effectively illustrating the characteristic in the configuration of Embodiment 2, spot radiography is firstly conducted to a subject, and then tomography is conducted. First, a subject is placed on a top board 2. When an operator instructs via the console 21 movement of the X-ray tube 3 and the FPD 4, the X-ray tube 3 and the FPD 4 each move to a position identical in body axis direction of the subject M. A portion of the subject M between the X-ray tube 3 and the FPD 4 is a site of interest of the subject M fluoroscoped through spot radiography.

When the operator instructs start of spot radiography through the console 21, the X-ray apparatus 1 goes into a spot radiography mode. Then, the X-ray tube controller 6 acquires a parameter for spot radiography from the memory 23. The amplifier array controller 45 acquires an analog gain for spot radiography from the memory 23. Accordingly, the image generation section 11 generates a fluoroscopic image P with a high contrast using radiation of relatively high intensity, and a display unit 22 displays it.

Subsequently, when the operator provides instructions on starting tomography of the subject through the console 21, the X-ray apparatus 1 switches to tomography mode. Then, the X-ray tube controller 6 acquires a parameter for tomography from the memory 23. The amplifier array controller 45 acquires an analog gain for tomography from the memory 23. Conventionally, radiation of relatively low intensity is adopted, and thus a fluoroscopic image with a low contrast should be obtained. However, an analog gain the amplifier array controller 45 acquires is higher than that upon spot radiography. Accordingly, original signals outputted from the transistors 41t are amplified by a high amplification factor, and a fluoroscopic image with a high contrast is generated in the image generation section 11. As shown in table T in FIG. 4, an analog gain in the tomography mode is 10 times. The X-ray tube 3 and the FPD 4 move in opposite directions to each other along the body axis A of the subject to obtain two or more like angle images.

Figure 12:
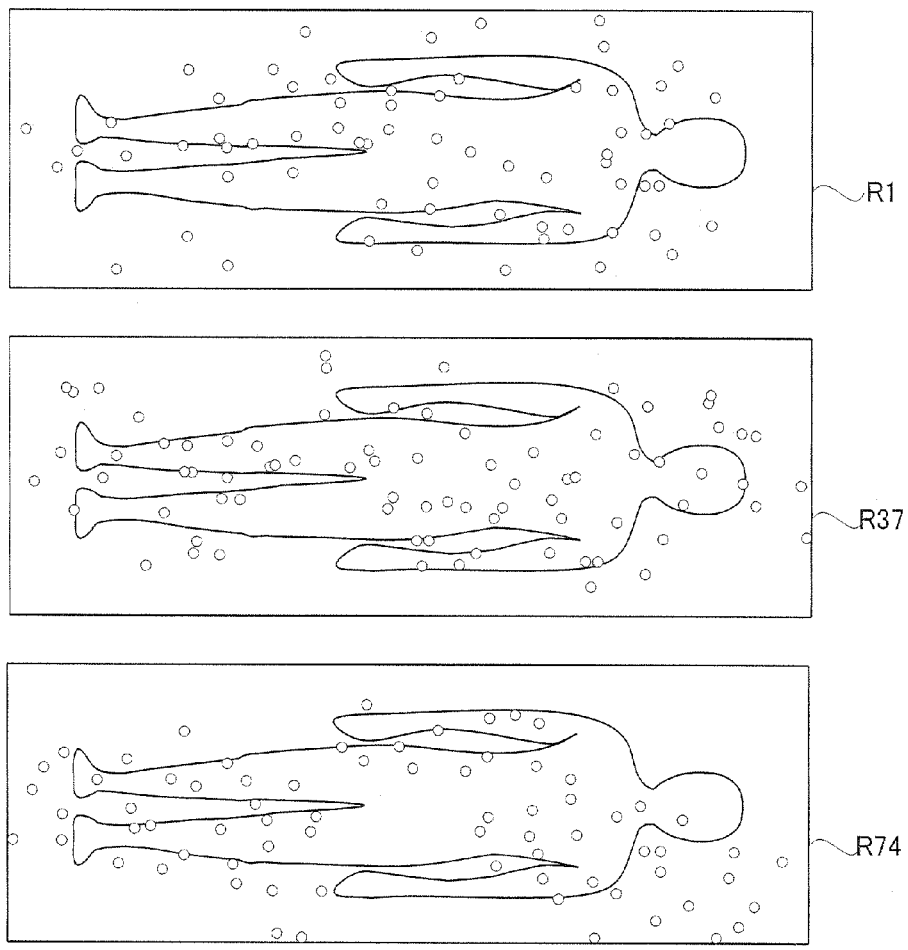
Figure 13:
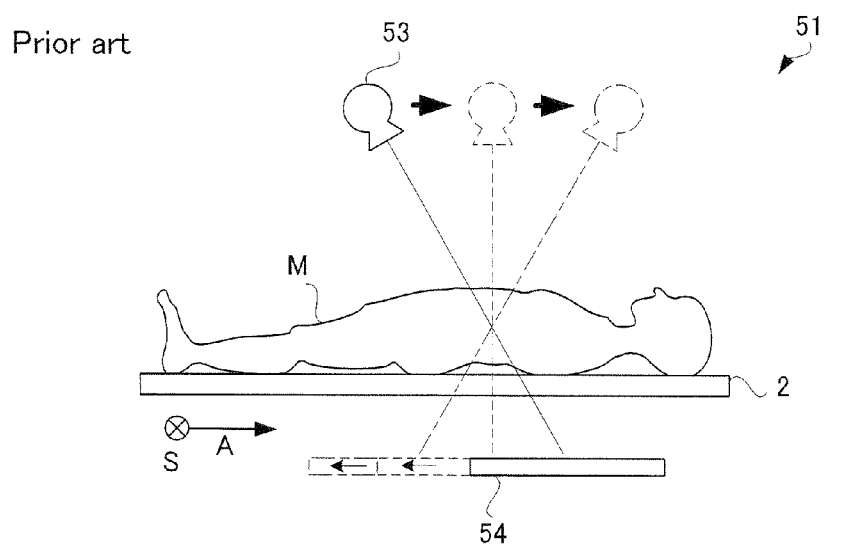
FIG. 13 is a functional block diagram showing a configuration of radiographic apparatus.

A noise component (false image) superimposed on the original signals appears in the like angle image R amplified by a high amplification factor. Specifically, as shown in FIG. 12, a granular false image appears in each like angle image R. Even when this is under spot radiography, the granular false image will not be removed. On the other hand, in tomography, a false image is to be removed during superimposing of the fluoroscopic images P. The like angle images R differ from one another in pattern of the granular false image because the false image superimposed on the original signal varies temporally. Such granular false image is cancelled when the superimposing section 12 superimposes the like angle images R. Accordingly, no influence of the noise appears in the tomographic image C. In this way, the tomographic image C superior to visibility is displayed on the display unit 22. Here, a region illustrated by shading in FIG. 12 is a fluoroscoped image of the subject appearing in the like angle image R.

Similar to Embodiment 1, output of single shot X-rays from the X-ray tube 3 in the tomography mode in Embodiment 2 is controlled to an intensity where no amplification of the amplifier array 44 is saturated.

As noted above, the X-ray apparatus I according to Embodiment 1 may select the spot radiography mode or the tomography mode. Moreover, the FPD 4 provided in the X-ray apparatus 1 according to Embodiment 1 converts X-rays into electric signals, and thereafter amplifies the signals to output them to the image generation section 11. In the conventional configuration, the original signal is amplified by a given analog gain regardless of the imaging mode. On the other hand, according to Embodiment 1, the analog gain in tomography mode is higher than that in spot radiography mode. Consequently, a fluoroscopic image P obtained in the tomography mode has a higher contrast even when a dose of radiation is suppressed in the tomography mode.

Generally, an increased analog gain may lead to amplified noise components superimposed on the original signal. When a fluoroscopic image P is obtained with the X-ray apparatus 1 of Embodiment 1, a false image due to noise components will surely appear with ease as illustrated in FIG. 6. The tomographic image C, however, is obtained through superimposing two or more fluoroscopic images P (or the like angle images R). In comparison of the fluoroscopic images P (or the like angle images R), they differ from one another in appearance of the false image. Accordingly, superimposing these images may achieve cancel of the false images. In this way, a tomographic image C finally obtained has no false image. The fluoroscopic images differ from one another in appearance of the false image because the noise component superimposed on the original signal varies temporally and two or more fluoroscopic P images are each obtained with different timing. The false image appearing in the strip-shaped image is to be cancelled, since the strip-shaped images forming the like angle image R are each obtained with different timing.

Since the spot radiography is conducted with a low analog gain and sufficiently high intensity of radiation as usual, the fluoroscopic image P in the spot radiography is clear with no false image appearing therein.

Moreover, output of single-shot radiation from the X-ray tube 3 is less in the tomography mode than in the spot radiography mode. Accordingly, exposure radiation to the subject M may be minimized in the tomography mode. Here, two or more fluoroscopic images P are superimposed to generate the tomographic image C. Consequently, there is no problem even when each fluoroscopic image P contains some false images.

According to the foregoing configuration, amplification of an electric signal is performed prior to digital conversion. Here, the electric signal prior to amplification is analog data. Consequently, amplification of data in an analog format may achieve faithful amplification of the original signal. Moreover, once digital processing is performed, data processing subsequent to the image generation section 11 may be simplified, and deterioration with data transmission may be avoided as much as possible.

Moreover, with the foregoing configuration, the tomography mode or the spot radiography mode may be selected from the operator's instructions. When the operator selects either of the modes, an analog gain will be changed accordingly. Therefore, the operator may take images regardless of the analog gain.

Moreover, the X-ray tube controller 6 sets output of single-shot radiation from the X-ray tube 3 in the tomography mode to an intensity where no amplification of the amplifier array 44 is saturated. With this configuration, the lower limit of X-ray output in the tomography mode may be defined. The lower X-ray output from the X-ray tube 3 is, the higher the amplification factor of the amplifier array 44 becomes. If the X-ray output is extremely low, amplification of the amplifier array 44 is saturated. Consequently, the contrast in the image becomes unclear. According to the foregoing configuration, tomography is conducted with a sufficient intensity of X-rays so as not to introduce such saturation phenomenon. As a result, a tomographic image may be obtained suitable for diagnosis.

This invention is not limited to the foregoing embodiment, but may be modified as follows:

(1) Each foregoing embodiment discusses medical apparatus. This invention is applicable also to apparatus for industrial use and for the nuclear field.

(2) X-rays used in each foregoing embodiment are an example of radiation in this invention. Therefore, this invention may be adapted also for radiation other than X-rays.

INDUSTRIAL UTILITY

As described above, this invention is suitable for radiographic apparatus for medical uses.

The invention claimed is:
1. Radiographic apparatus comprising:
a radiation source for emitting radiation;
a radiation source controlling device for controlling output of radiation;
a radiation detecting device for detecting radiation;
a moving device for moving the radiation source and the radiation detecting device synchronously;
an image generation device for generating a fluoroscopic image based on a detection signal from the radiation detecting device; and
a superimposing device for superimposing a series of fluoroscopic images continuously taken while the radiation source and the radiation detecting device moves or superimposes an identical site of the subject in the series of fluoroscopic images one another, thereby generating a tomographic image,
the radiation detecting device comprising:
(A) a radiation conversion device for converting radiation entering the radiation detecting device into an electric signal; and
(B) an amplifying device for amplifying the electric signal by a given amplification factor,
wherein letting an imaging mode where the radiation detecting device is irradiated with single shot radiation to obtain a single fluoroscopic imaging be a spot radiography mode, and an imaging mode where a tomographic image is obtained be a tomography mode, an amplification factor is higher in the tomography mode than in the spot radiography mode, and output of single-shot radiation from the radiation source is less in the tomography mode than in the spot radiography mode.

2. The radiographic apparatus according to claim 1, wherein
the moving device moves the radiation source and the radiation detecting device synchronously in opposite directions to each other, and
the superimposing device superimposes a series of fluoroscopic images to generate a tomographic image.

3. The radiographic apparatus according to claim 1, wherein
the moving device moves the radiation source and the radiation detecting device synchronously in an identical direction to each other,
a like angle image generation device is further included that divides a series of the fluoroscopic images into strips to generate strip-shaped images, and selects and joins the strip-shaped images having an equal angle of X-ray radiation to the radiation detecting device to obtain two or more like angle images, and the superimposing device superimposes a series of the like angle images to form a tomographic image.

4. The radiographic apparatus according to claim 1, wherein the amplifying device is formed of an analog amplifier and includes an A/D converter that converts output of the amplifying device as analog data into digital data.

5. The radiographic apparatus according to claim 1, wherein an input unit is further provided for inputting operators instructions that allows variation in imaging mode.

6. Radiographic apparatus comprising:

a radiation source for emitting radiation;

a radiation source controlling device for controlling output of radiation;

a radiation detecting device for detecting radiation;

a moving device for moving the radiation source and the radiation detecting device synchronously;

an image generation device for generating a fluoroscopic image based on a detection signal from the radiation detecting device; and a superimposing device for superimposing a series of fluoroscopic images continuously taken while the radiation source and the radiation detecting device moves or superimposes an identical site of the subject in the series of fluoroscopic images one another, thereby generating a tomographic image, the radiation detecting device comprising:

(A) a radiation conversion device for converting radiation entering the radiation detecting device into an electric signal;

(B) an amplifying device for amplifying the electric signal by a given amplification factor; and (C) an amplification factor setting device for setting an amplification factor of the amplifying device in accordance with an imaging mode upon imaging, letting an imaging mode that irradiates the radiation detecting device with single shot radiation to obtain a single fluoroscopic imaging be a spot radiography mode and letting an imaging mode that obtains a tomographic image be a tomography mode, wherein the amplification factor setting device sets an amplification factor in the tomography mode higher than that in the spot radiography mode, and the radiation source controlling device sets output of single-shot radiation from the radiation source less in the tomography mode than in the spot radiography mode and to an intensity where no amplification of the amplifying device is saturated.

7. The radiographic apparatus according to claim 6, wherein the moving device moves the radiation source and the radiation detecting device synchronously in opposite directions to each other, and the superimposing device superimposes a series of fluoroscopic images to generate a tomographic image.

8. The radiographic apparatus according to claim 6, wherein the moving device moves the radiation source and the radiation detecting device synchronously in an identical direction to each other, a like angle image generation device is further included that divides a series of the fluoroscopic images into strips to generate strip-shaped images, and selects and joins the strip-shaped images having an equal angle of X-ray radiation to the radiation detecting device to obtain two or more like angle images, and the superimposing device superimposes a series of the like angle images to form a tomographic image.

9. The radiographic apparatus according to claim 6, wherein the amplifying device is formed of an analog amplifier and includes an A/D converter that converts output of the amplifying device as analog data into digital data.

10. The radiographic apparatus according to claim 6, wherein an input unit is further provided for inputting operators instructions that allows variation in imaging mode.

* * * * *